(12) United States Patent
Acevedo-Duncan

(10) Patent No.: US 8,716,266 B2
(45) Date of Patent: May 6, 2014

(54) USE OF PKC-IOTA INHIBITORS FOR THE TREATMENT OF GLIOMA

(75) Inventor: Mildred E. Acevedo-Duncan, Plant City, FL (US)

(73) Assignees: University of South Florida, Tampa, FL (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/602,708

(22) Filed: Sep. 4, 2012

(65) Prior Publication Data

US 2013/0058932 A1    Mar. 7, 2013

Related U.S. Application Data

(60) Provisional application No. 61/530,051, filed on Sep. 1, 2011.

(51) Int. Cl.
*A61K 31/675*    (2006.01)

(52) U.S. Cl.
USPC .............................................. 514/94; 514/44

(58) Field of Classification Search
USPC ............................................ 514/94, 44 A, 44
See application file for complete search history.

(56) References Cited

U.S. PATENT DOCUMENTS 7,482,131 B2 *   1/2009   Acevedo-Duncan et al. ............................ 435/7.23

OTHER PUBLICATIONS

Phillai et al., The International Journal of Biochemistry and Cell Biology, Feb. 16, 2011, 43:784-794.*
Patel et al., Cell Proliferation, 2008, 41:122-135.*

* cited by examiner

*Primary Examiner* — Rei-tsang Shiao

(74) *Attorney, Agent, or Firm* — Saliwanchik, Lloyd & Eisenschenk

(57) ABSTRACT

The present invention pertains to use of PKC-iota inhibitors for treatment of glioma. In a specific embodiment, the treatment method comprises administering ICA-1 or a salt thereof to a subject with glioma. In another embodiment, the treatment method comprises contacting glioma cells with an effective amount of ICA-1 or a salt thereof.

9 Claims, 2 Drawing Sheets

USE OF PKC-IOTA INHIBITORS FOR THE TREATMENT OF GLIOMA

CROSS-REFERENCE TO RELATED APPLICATION

This application claims the benefit of U.S. provisional application Ser. No. 61/530,051, filed Sep. 1, 2011, which is herein incorporated by reference in its entirety.

BACKGROUND OF THE INVENTION

Gliomas are tumors that arise from glial cells, such as astrocytes, oligodendrocytes, and ependymal cells. Gliomas account for about 32% of brain tumors and 80% of malignant brain tumors. High grade (i.e. malignant) gliomas are highly lethal. Median patient survival is less than one year despite a combination of rigorous therapies including surgery, radiation, chemotherapy, and anti-tumor medications.

While therapies such as post-operative radiation may delay tumor regrowth and prolong survival, complete tumor control has rarely been achieved. This is due, at least in part, to the abundance of hypoxic or tumor stem cells, the rapidity of glioma proliferation, their low radiosensitivity, and the rapid emergence of resistant cells. Accordingly, there is a critical need for developing improved therapy for glioma.

BRIEF SUMMARY OF THE INVENTION

The present invention provides methods for treatment of glioma. In one embodiment, the method comprises administering, to a subject in need of such treatment, an effective amount of a PKC-iota (PKC-ι) inhibitor. PKC-ι inhibitors useful according to the present invention include, but are not limited to, agents that inhibit PKC-ι activity; and agents that reduce or inhibit the expression of PKC-iota.

The present invention can be to treat glioma types including, but not limited to, astrocytic tumors including anaplastic astrocytoma, glioblastoma, and glioblastoma multiform; oligodendroglial tumors; gliomas containing different types of glial cells, such as oligoastrocytoma and oligodendroglioma.

In a specific embodiment, the method for treating glioma comprises administering, to a subject in need of such treatment, an effective amount of a compound of Formula (I), or a salt thereof. In a specific embodiment, the method comprises administering ICA-1 or a salt thereof to a subject with glioma. In a specific embodiment, the compound of Formula (I) (such as ICA-1), or a salt thereof, is administered via injection into the glioma site.

In another embodiment, the method comprises contacting glioma cells with an effective amount of a PKC-ι inhibitor, such as a compound of Formula (I), or a salt thereof.

BRIEF DESCRIPTION OF THE SEQUENCE

SEQ ID NO: 1 is an amino acid sequence of human protein kinase C-iota (PKC-ι).
SEQ ID NO: 2 5'-CAAGCCAAGCGUUUCAACA-3' is a single strand of PKC-ι siRNA.
SEQ ID NO: 3 5'-UGUUGAAACGCUUGGCUUG-3' is a single strand of PKC-ι siRNA.
SEQ ID NO: 4 5'-GGAACGAUUGGGUUGUCAU-3' is a single strand of PKC-ι siRNA.
SEQ ID NO: 5 5'-AUGACAACCCAAUCGUUCC-3' is a single strand of PKC-ι siRNA.
SEQ ID NO: 6 5'-CCCAAUAUCUUCUCUUGUA-3' is a single strand of PKC-ι siRNA.
SEQ ID NO: 7 5'-UACAAGAGAAGAUAUUGGG-3' is a single strand of PKC-ι siRNA.

DETAILED DISCLOSURE OF THE INVENTION

The present invention provides methods for treatment of glioma. In one embodiment, the method comprises administering, to a subject in need of such treatment, an effective amount of a PKC-iota (PKC-ι) inhibitor. PKC-ι inhibitors useful according to the present invention include, but are not limited to, agents that inhibit PKC-ι activity; and agents that reduce or inhibit the expression of PKC-iota.

The present invention can be to treat glioma types including, but not limited to, astrocytic tumors including astrocytoma, anaplastic astrocytoma, glioblastoma, and glioblastoma multiform; oligodendroglial tumors; and gliomas containing different types of glial cells, such as oligoastrocytoma and oligodendroglioma.

In a specific embodiment, the method for treating glioma comprises administering, to a subject in need of such treatment, an effective amount of a compound of Formula (I), or a salt thereof. In a specific embodiment, the method comprises administering ICA-1 or a salt thereof to a subject with glioma. In a specific embodiment, the compound of Formula (I) (such as ICA-1), or a salt thereof, is administered via injection into the glioma site.

In another embodiment, the method comprises contacting glioma cells with an effective amount of a PKC-ι inhibitor, such as a compound of Formula (I), or a salt thereof.

PKC-ι Inhibitors

In one embodiment, the present invention pertains to uses of PKC-ι inhibitors for treatment of glioma. PKC-ι inhibitors useful according to the present invention include, but are not limited to, agents that inhibit PKC-ι activity; and agents that reduce or inhibit the expression of PKC-iota, such as agents that inhibit the transcription, translation, and/or processing of PKC-iota.

Agents that inhibit PKC-ι activity include, but are not limited to, anti-PKC-ι antibodies, aptamers, PKC-ι binding partners, and small molecule inhibitors of PKC-ι.

In an embodiment, the PKC-ι inhibitor is 1H-imidazole-4-carboxamide, 5-amino-1-[2,3-dihydroxy-4-[(phosphonooxy)methyl]cyclopentyl]-[1R-(1α, 2β, 3β, 4α)] (ICA-1), or a salt thereof. ICA-1 has the following structure:

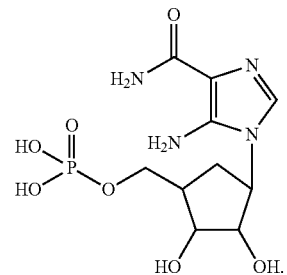 [SMILES: NC(=O)c1ncn(C2CC(COP(=O)(O)O)C(O)C2O)c1N]

Figure 2:
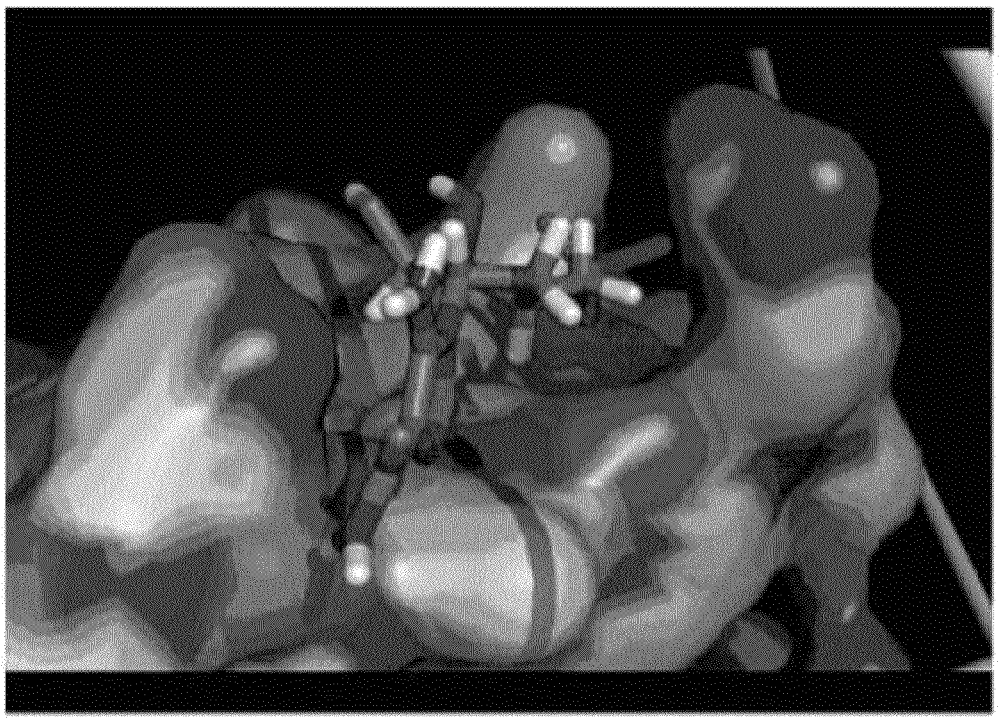
FIG. 2 displays the molecular docking of ICA-1 on amino acid residues 469-475 of the catalytic domain of PKC-ι.

ICA-1 binds to the catalytic domain of human PKC-ι (SEQ ID NO:1, GenBank Accession No. AAB17011) at amino acid residues 469-475 (glutamine-469, isoleucine-470, arginine-471, isoleucine-472, proline-473, arginine-474, serine-475). Based on the molecular docking of ICA-1 on amino acid residues 469-475 of the catalytic domain of PKC-ι as shown in FIG. 2, the present invention further contemplates use of compounds of Formula I, or any salt thereof, for treating glioma. The compounds of Formula I include ICA-1 as well as ester, ether, and alkyl substituted derivatives of ICA-1, having the following structure:

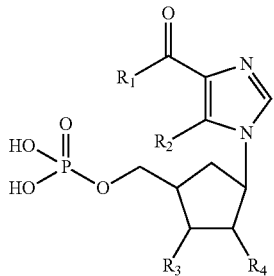

wherein $R_1$ and $R_2$ are, independently, —$NH_2$ or alkylamino; and wherein $R_3$ and $R_4$ are, independently, —H, —OH, alkoxy, or —OC(O)R', wherein R' is linear saturated monovalent radicals of one to four carbon atoms or a branched saturated monovalent of three or four carbon atoms.

"Alkyl," as used herein, refers to linear saturated monovalent radicals of one to eight carbon atoms or a branched saturated monovalent of three to eight carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Alkylamino," as used herein, refers to a radical —NHR or —$NR_2$ where each R is independently an alkyl group. Examples include methylamino, (1-methylethyl)amino, methylamino, dimethylamino, methylethylamino, di(1-methyethyl)amino, and the like.

"Alkoxy," as used herein, refers to the radical —$OR_a$, where $R_a$ is an alkyl group. Exemplary alkoxy groups include methoxy, ethoxy, propoxy, and the like.

"Carboalkoxy," as used herein, refers to a radical —C(O)R where R is, for example, hydrogen, alkyl or cycloalkyl, heterocycloalkyl, or alkyl halo.

"Halo," as used herein, refers to fluoro, chloro, bromo, or iodo.

"Haloalkyl," as used herein, refers to alkyl substituted with one or more same or different halo atoms, e.g., —$CH_2Cl$, —$CH_2Br$, —$CF_3$, —$CH_2CH_2Cl$, —$CH_2CCl_3$, and the like.

The compounds of Formula I bind to PKC-ι, preferably, amino acid residues 469-475 of human PKC-ι of SEQ ID NO: 1.

In one embodiment, the PKC-ι inhibitor is an antibody, aptamer, or binding partner that binds to PKC-ι. In a specific embodiment, the PKC-ι inhibitor is an antibody, aptamer, or binding partner that binds specifically to PKC-ι. In a further specific embodiment, the PKC-ι inhibitor is an antibody, aptamer, or binding partner that binds specifically to human PKC-ι. In a further specific embodiment, the PKC-ι inhibitor is an antibody, aptamer, or binding partner that binds specifically to a human PKC-ι of SEQ ID NO:1. In some embodiments, the PKC-ι inhibitor is an antibody, aptamer, or binding partner that binds to a PKC-ι protein or polypeptide comprising an amino acid sequence having at least 90%, 95%, 96%, 97%, 98%, 99%, or 100% identity to SEQ ID NO:1, wherein the PKC-ι protein or polypeptide comprises a catalytic domain that corresponds to amino acid residues 469-475 of SEQ ID NO:1 (glutamine-469, isoleucine-470, arginine-471, isoleucine-472, proline-473, arginine-474, serine-475).

In certain embodiments, the PKC-ι inhibitor is an antibody, aptamer, or binding partner that binds specifically to a PKC-ι protein of non-human animal species including, but not limited to, apes, chimpanzees, orangutans, monkeys, dogs, cats, horses, pigs, sheep, goats, chickens, mice, rats, and guinea pigs. Antibodies that bind specifically to PKC-ι proteins are commercially available. In one embodiment, the PKC-ι inhibitor is an anti-PKC-ι monoclonal antibody manufactured by BD TRANSDUCTION LABORATORIES, San Diego, Calif. (Product No. 610175). The skilled artisan can readily make antibodies, aptamers, or binding partners that specifically bind to PKC-ι proteins that are publically known. In another embodiment, the PKC-ι inhibitor is a fusion construct comprising the antibody, aptamer, or binding partner that binds specifically to a PKC-ι protein (such as human PKC-ι). "Specific binding" or "specificity" refers to the ability of a protein to detectably bind an epitope presented on a protein or polypeptide molecule of interest, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific target molecule versus nonspecific binding to other irrelevant molecules.

Anti-PKC-ι antibodies of the present invention can be in any of a variety of forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art; see, e.g., Hudson and Kortt, J. Immunol. Methods 231:177 189, 1999); fusion constructs containing an antibody or antibody fragment; and human or humanized immunoglobulin molecules or fragments thereof.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the present invention include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature*, 1975, 256:495-497, the disclosure of which is herein incorporated by reference. An exemplary hybridoma technology is described by Niman et al., *Proc. Natl. Acad. Sci. U.S.A.*, 1983, 80:4949-4953. Other methods of producing monoclonal antibodies, a hybridoma cell, or a hybridoma cell culture are also well known. See e.g., Antibodies: A Laboratory Manual, Harlow et al., Cold Spring Harbor Laboratory, 1988; or the method of isolating monoclonal antibodies from an immunological repertoise as described by Sasatry, et al., *Proc. Natl. Acad. Sci. USA,* 1989, 86:5728-5732; and Huse et al., *Science,* 1981, 246:1275-1281. The references cited are hereby incorporated herein by reference.

In one embodiment of the invention, monoclonal antibodies specific for PKC-ι can be used as a delivery vehicle for drug or toxin. Drug or toxin can be conjugated to the antibodies using a biochemical approach. Monoclonal antibodies specific for the amino-terminus of PKC-ι can be used as a delivery vehicle for drug or toxin. This enables the transport of drug or toxin to tumor cells with high expression of PKC-ι.

In some embodiments, PKC-ι inhibitors useful according to the present invention are agents that reduce or inhibit the expression of PKC-iota, such as agents that inhibit the transcription, translation, and/or processing of PKC-iota.

In an embodiment, the PKC-ι inhibitor is a PKC-ι antisense polynucleotide. In an embodiment, the PKC-ι inhibitor is an antisense polynucleotide that targets human PKC-ι mRNA. In some embodiments, the PKC-ι antisense polynucleotides target PKC-ι mRNAs of non-human animals including, but not limited to, apes, chimpanzees, orangutans, monkeys, dogs, cats, horses, pigs, sheep, goats, chickens, mice, rats, and guinea pigs. The skilled artisan would readily appreciate that the antisense polynucleotides can be designed to target any PKC-ι mRNAs publically known.

In some embodiments, the PKC-ι inhibitor is a siRNA having a sequence sufficiently complementary to a target PKC-ι mRNA sequence to direct target-specific RNA interference (RNAi). In some embodiments, the PKC-ι inhibitor is siRNA having a sequence sufficiently complementary to a target human PKC-ι mRNA sequence (such as mRNA encoding SEQ ID NO:1) to direct target-specific RNA interference.

In some embodiments, the PKC-ι inhibitor is a siRNA having a sequence sufficiently complementary to a target PKC-ι mRNA sequence, wherein the target PKC-ι mRNA sequence encodes a naturally-occurring or recombinant form of a PKC-ι polypeptide comprising an amino acid sequence having at least 90%, 95%, 96%, 97%, 98%, 99%, or 100% identity to SEQ ID NO:1, wherein the PKC-ι polypeptide comprises a catalytic domain that corresponds to amino acid residues 469-475 of SEQ ID NO:1 (glutamine-469, isoleucine-470, arginine-471, isoleucine-472, proline-473, arginine-474, serine-475).

Examples of siRNA that target human PKC-ι mRNA include SEQ ID NOs: 2-7.

Examples of antisense polynucleotides include, but are not limited to, single-stranded DNAs and RNAs that bind to complementary target PKC-iota mRNA and inhibit translation and/or induce RNaseH-mediated degradation of the target transcript; siRNA oligonucleotides that target or mediate PKC-ι mRNA degradation; ribozymes that cleave PKC-ι mRNA transcripts; and nucleic acid aptamers and decoys, which are non-naturally occurring oligonucleotides that bind to and block PKC-ι protein targets in a manner analogous to small molecule drugs.

The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as PKC-ι.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA (e.g., PKC-ι mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

The present invention also contemplates vectors (e.g., viral vectors) and expression constructs comprising the nucleic acid molecules useful for inhibiting PKC-ι expression and/or activity. In an embodiment, the vector comprises a siRNA that targets PKC-ι mRNA. In another embodiment, the vector comprises a nucleic acid molecule encoding an anti-PKC-ι antibody.

As used herein, the term "expression construct" refers to a combination of nucleic acid sequences that provides for transcription of an operably linked nucleic acid sequence. As used herein, the term "operably linked" refers to a juxtaposition of the components described, wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

Treatment of Glioma

The present invention provides methods for treatment of glioma. In one embodiment, the method comprises administering, to a subject in need of such treatment, an effective amount of a PKC-iota (PKC-ι) inhibitor.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression and/or severity of an undesired physiological change or a diseased condition. For instance, treatment includes, for example, slowing the growth and/or proliferation of glioma cells; reducing glioma size; alleviating symptoms associated with glioma (such as headaches, seizure, loss of vision, and pain); and prolonging patient survival.

The term "effective amount," as used herein, refers to an amount that is capable of treating or ameliorating a disease or condition or otherwise capable of producing an intended therapeutic effect. In certain embodiments, the effective amount enables a 5%, 10%, 20%, 30%, 40%, 50%, 75%, 90%, 95%, 99% or 100% reduction in glioma size.

The term "subject," as used herein, describes an organism, including mammals such as primates, to which treatment with the compositions according to the present invention can be administered. Mammalian species that can benefit from the disclosed methods include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

In an embodiment, subjects in need of such treatment are diagnosed with glioma. By way of example, glioma can be identified by routine diagnostic or screening techniques such as magnetic resonance imaging (MRI), CT scan, etc.

In some embodiments, the present invention can be used to treat glioma types including, but not limited to, astrocytic tumors including astrocytoma, anaplastic astrocytoma, glioblastoma, and glioblastoma multiform; oligodendroglial tumors; and gliomas containing different types of glial cells, such as oligoastrocytoma, anaplastic oligodendroglioma, and oligodendroglioma.

In addition, the present invention can be used to treat both benign and malignant gliomas. In an embodiment, the present invention can be used to treat gliomas that originate from the brain. In another embodiment, the present invention can be used to treat gliomas that originate from the spinal cord.

In some embodiments, the present invention can be used to treat Grade I, II, III, or IV glioma including, but not limited to, Grade IV glioblastoma and glioblastoma multiform.

In a specific embodiment, the method for treating glioma comprises administering, to a subject in need of such treatment, an effective amount of a compound of Formula (I), or a salt thereof. In a specific embodiment, the method comprises administering ICA-1 or a salt thereof to a subject with glioma. In a specific embodiment, the compound of Formula (I) (such as ICA-1), or a salt thereof, is administered via injection into the glioma site.

In another embodiment, the method comprises contacting glioma cells with an effective amount of a PKC-ι inhibitor, such as a compound of Formula (I), or a salt thereof.

In a further embodiment, the therapeutic methods of the present invention are applied in combination with one or more conventional therapies for glioma, such as surgery, chemotherapy, and radiation therapy. In an embodiment, the present invention comprises administering a PKC-ι inhibitor to a subject with glioma, before surgery and/or radiation therapy. In another embodiment, the present invention comprises administering a PKC-ι inhibitor to a subject with glioma, wherein the subject received surgery and/or radiation therapy.

Therapeutic Compositions and Formulations

The present invention further provides therapeutic compositions that contain an effective amount of a therapeutic agent and a pharmaceutically acceptable carrier or adjuvant.

The therapeutic agent can be formulated in a variety of forms. These include for example, solid, semi-solid, and liquid dosage forms, such as tablets, pills, powders, liquid solutions or suspensions, suppositories, and injectable and infusible solutions. The preferred form depends on the intended mode of administration and therapeutic application.

In a preferred embodiment, the composition is formulated in accordance with routine procedures as a pharmaceutical composition adapted for local injection administration to human beings. Typically, compositions for local injection administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The present invention also provides for a therapeutic method by administering therapeutic or pharmaceutical compositions in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil; vegetable oil such as peanut oil, soybean oil, and sesame oil; animal oil; or oil of synthetic origin.

Suitable carriers also include ethanol, dimethyl sulfoxide, glycerol, silica, alumina, starch, sorbitol, inosital, xylitol, D-xylose, manniol, powdered cellulose, microcrystalline cellulose, talc, colloidal silicon dioxide, calcium carbonate, magnesium cabonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic composition, if desired, can also contain minor amounts of wetting or emulsifying agents, or pH buffering agents.

The amount of active ingredient that may be combined with the carrier materials to produce a single dosage form will vary, depending such as the type of the condition and the subject to be treated. The amount of active ingredient that may be combined with the carrier materials to produce a single dosage form will vary, depending such as the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The therapeutic agents of the invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the present invention.

The therapeutic or pharmaceutical compositions of the present invention can also be formulated as neutral or salt forms. Pharmaceutically acceptable salts include, but are not limited to, hydrochloric, phosphoric, acetic, oxalic, sodium, potassium, ammonium, calcium, ferric hydroxides, isopropylamine, and triethylamine salts.

Routes of Administration

The therapeutic agents and compositions of the present invention can be administered to the subject being treated by standard routes, including oral, or parenteral administration including intravenous, intramuscular, and intraspinal injection, infusion, and electroporation, as well as co-administration as a component of any medical device or object to be inserted (temporarily or permanently) into a subject. In a preferred embodiment, the therapeutic agents and compositions of the present invention are administered via injection to the site of glioma.

In some embodiments, the methods disclosed herein include contacting a glioma or target glioma cell with an effective amount of a PKC-ι inhibitor. In some embodiments, the PKC-ι inhibitor comprises a polynucleotide (including recombinant expression vectors encoding PKC-ι antisense RNA, intracellular PKC-ι antibodies). In some embodiments, the therapeutic agents can be introduced into cells of the glioma using methods known in the art for introducing polynucleotides (e.g., DNA, RNA or the like) into cells in vivo. Examples of such methods encompass both non-viral and viral methods, including but not limited to, direct injection; receptor-Mediated DNA uptake; retroviral, adenoviral, and lentiviral therapy.

The amount of the therapeutic or pharmaceutical composition of the present invention effective in the treatment of glioma will depend on a variety of factors, such as the route of administration and the seriousness of the condition, and should be decided according to the judgment of the practitioner and each patient's circumstances. In general, the dosage ranges from about 0.01 µg/kg to about 10 mg/kg, about 0.01 µg/kg to about 1 mg/kg, about 0.01 µg/kg to about 100 µg/kg, about 0.01 µg/kg to about 10 µg/kg, or about 0.01 µg/kg to about 1 µg/kg. Such a unit dose may be administered once to several times (e.g. two, three and four times) every two weeks, every week, or every day.

In one embodiment, the therapeutic agents and compositions of the present invention and any second therapeutic agent are administered simultaneously or sequentially to the patient, with the second therapeutic agent being administered before, after, or both before and after treatment with the compounds of the present invention. Sequential administration may involve treatment with the second therapeutic agent on the same day (within 24 hours) of treatment with the subject compound. Sequential administration may also involve continued treatment with the second therapeutic agent on days that the subject compound is not administered.

Following is an example that illustrates procedures and embodiments for practicing the invention. The example should not be construed as limiting. All percentages are by weight and all solvent mixture proportions are by volume unless otherwise noted.

EXAMPLE 1

Treatment of Glioma Using an PKC-Iota Inhibitor—ICA-1

This Example shows that PKC-iota inhibitors, such as ICA-1, can be used to prevent and/or treat glioma. Briefly, nine female athymic nude mice, weighing 17 to 23 grams, were divided into 3 groups: Group 1, mice received human glioblastoma xenografts and were treated with saline controls (n=3); Group 2, mice received human glioblastoma xenografts and were treated with ICA-1 (80 mg/kg/day; 20 µM) immediately after glioma implantation (n=3); Group 3, mice received human glioblastoma xenografts and were treated with ICA-1 (80 mg/kg/day, 20 µM) when the tumor reached 100 mm$^3$ on day 5 post implantation (n=3).

Human glioblastoma cell line U-87 MG, a commonly-studied human grade IV glioblastoma-astrocytoma, epithelial-like cell line, was injected subcutaneously into right flank ($1\times10^6$ cells/flank in 0.1 ml PBS) of the mice. The cell injection site was marked. After glioblastoma implantation, ICA-1 (80 mg/kg/day; 20 µM) was subcutaneously injected, daily, into and around the tumor/cell injection area of Groups 2 and 3 mice; Group 1 mice was treated with vehicle. Tumor volume was calculated using the following formula: length×width×width×½.

The results showed that ICA-1 prevented tumor growth in both Group 2 and Group 3 mice. However, Group 2 mice lost significant weight and died seven days post ICA-1 treatment, indicating that a daily dosage of 80 mg/kg/day was lethal to mice (data not shown).

Figure 1A:
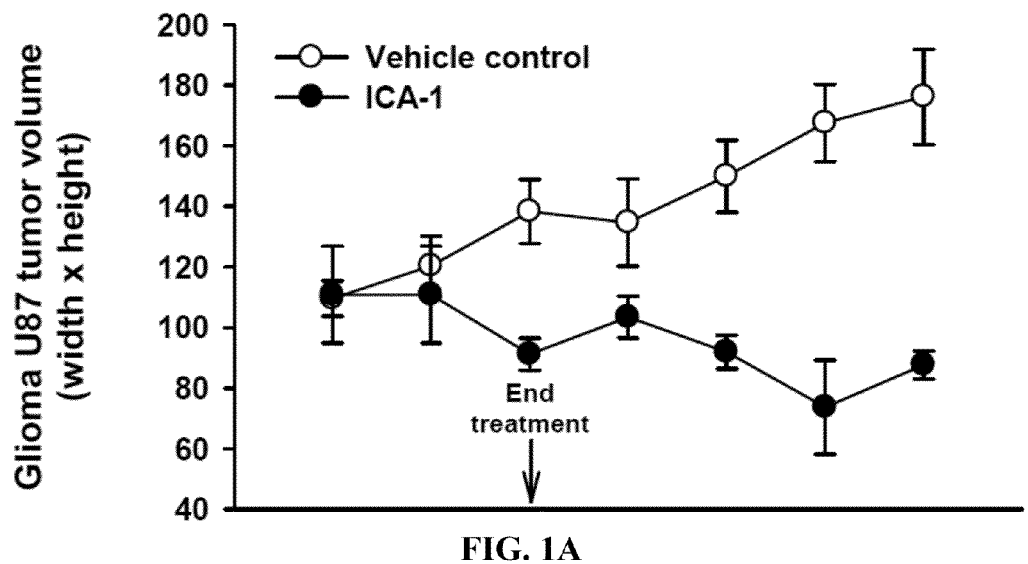
FIG. 1 shows the effects of ICA-1 on preventing or reducing glioma growth. Open squares represent mice that received glioma xenografts and were treated with saline controls (n=3). Filled circles represent mice that received glioma xenografts and were treated with ICA-1 (80 mg/kg/day) when the tumor reached 100 mm$^3$ on day 5 post implantation (n=2).
Figure 1B:
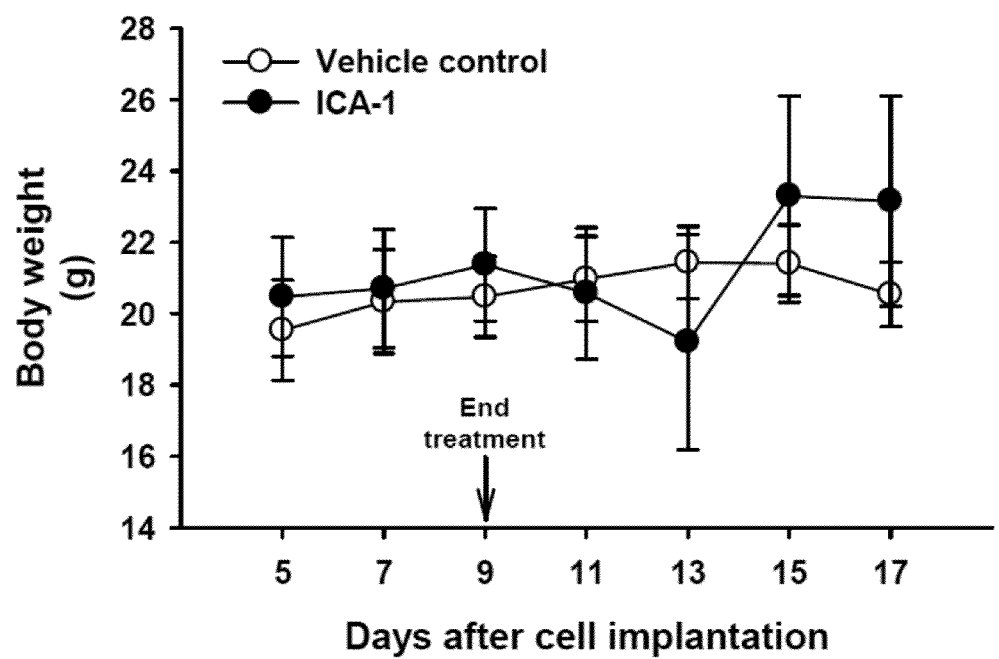

In Group 3 mice, the ICA-1 treatment only lasted for 4 days (from day 5-day 9 post glioma implantation), and was terminated on day 9 post glioma implantation (FIG. 1A; filled circles). As shown in FIG. 1A, the ICA-1 treatment reduced glioma volume. Further, the glioma size continued to reduce after the ICA-1 treatment was terminated. By the end of the study period (8 days after the termination of the ICA-1 treatment), the glioma size of Group 3 mice was 53% of that of the control mice. Group 3 mice also did not exhibit significant weight loss (FIG. 1B; filled circles). The results show that inhibiting PKC-iota (e.g. via the administration of ICA-1) has preventive and/or treatment effects on glioma.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of treating glioma comprising administering, to a subject in need of such treatment, an effective amount of a PKC-iota inhibitor, and, optionally, a pharmaceutically acceptable carrier, wherein the PKC-iota inhibitor is
a compound of Formula (I) or a salt thereof, wherein the compound of formula (I) is:

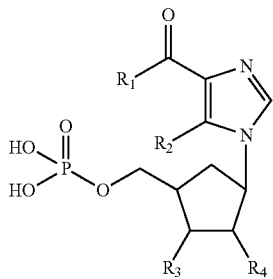

wherein $R_1$ and $R_2$ are, independently, —$NH_2$ or alkylamino, and
wherein $R_3$ and $R_4$ are, independently, —H, —OH, alkoxy, or —OC(O)R',
wherein R' is a linear saturated monovalent radical of one to four carbon atoms or a branched saturated monovalent of three or four carbon atoms.

2. The method of claim 1, wherein the subject is a human that has glioma.

3. The method of claim 1, wherein the PKC-iota inhibitor is 1H-imidazole-4-carboxamide, 5-amino-1-[2,3-dihydroxy-4-[(phosphonooxy)methyl]cyclopentyl]-[1R-(1α, 2β, 3β, 4α)] (ICA-1), or a salt thereof.

4. A method of inhibiting the proliferation of glioma cells, comprising administering to a glioma cell an effective amount of a PKC-iota inhibitor, and, optionally, a pharmaceutically acceptable carrier, wherein the PKC-iota inhibitor is
a compound of Formula (I) or a salt thereof, wherein the compound of formula (I) is:

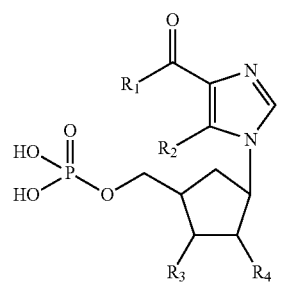

wherein $R_1$ and $R_2$ are, independently, —$NH_2$ or alkylamino, and wherein $R_3$ and $R_4$ are, independently, —H, —OH, alkoxy, or —OC(O)R', wherein R' is a linear saturated monovalent radical of one to four carbon atoms or a branched saturated monovalent of three or four carbon atoms.

5. The method of claim 4, wherein the PKC-iota inhibitor is 1H-imidazole-4-carboxamide, 5-amino-1-[2,3-dihydroxy-4-[(phosphonooxy)methyl]cyclopentyl]-[1R-(1α, 2β, 3β, 4α)] (ICA-1), or a salt thereof.

6. The method of claim 1, wherein the subject has a brain glioma.

7. The method of claim 3, wherein the subject has a brain glioma.

8. The method of claim 4, comprising administering to a brain glioma cell an effective amount of a PKC-iota inhibitor.

9. The method of claim 5, comprising administering to a brain glioma cell an effective amount of a PKC-iota inhibitor.

* * * * *

```
                       SEQUENCE LISTING

<160> NUMBER OF SEQ ID NOS: 7

<210> SEQ ID NO 1
<211> LENGTH: 587
<212> TYPE: PRT
<213> ORGANISM: Homo sapiens

<400> SEQUENCE: 1

Met Ser His Thr Val Ala Gly Gly Ser Gly Asp His Ser His Gln
1               5                   10                  15

Val Arg Val Lys Ala Tyr Tyr Arg Gly Asp Ile Met Ile Thr His Phe
                20                  25                  30

Glu Pro Ser Ile Ser Phe Glu Gly Leu Cys Asn Glu Val Arg Asp Met
                35                  40                  45

Cys Ser Phe Asp Asn Glu Gln Leu Phe Thr Met Lys Trp Ile Asp Glu
    50                  55                  60

Glu Gly Asp Pro Cys Thr Val Ser Ser Gln Leu Glu Leu Glu Glu Ala
65                  70                  75                  80

Phe Arg Leu Tyr Glu Leu Asn Lys Asp Ser Glu Leu Leu Ile His Val
                85                  90                  95

Phe Pro Cys Val Pro Glu Arg Pro Gly Met Pro Cys Pro Gly Glu Asp
                100                 105                 110

Lys Ser Ile Tyr Arg Arg Gly Ala Arg Arg Trp Arg Lys Leu Tyr Cys
                115                 120                 125

Ala Asn Gly His Thr Phe Gln Ala Lys Arg Phe Asn Arg Arg Ala His
                130                 135                 140

Cys Ala Ile Cys Thr Asp Arg Ile Trp Gly Leu Gly Arg Gln Gly Tyr
145                 150                 155                 160

Lys Cys Ile Asn Cys Lys Leu Leu Val His Lys Lys Cys His Lys Leu
                165                 170                 175

Val Thr Ile Glu Cys Gly Arg His Ser Leu Pro Gln Glu Pro Val Met
                180                 185                 190

Pro Met Asp Gln Ser Ser Met His Ser Asp His Ala Gln Thr Val Ile
                195                 200                 205

Pro Tyr Asn Pro Ser Ser His Glu Ser Leu Asp Gln Val Gly Glu Glu
        210                 215                 220

Lys Glu Ala Met Asn Thr Arg Glu Ser Gly Lys Ala Ser Ser Ser Leu
225                 230                 235                 240

Gly Leu Gln Asp Phe Asp Leu Leu Arg Val Ile Gly Arg Gly Ser Tyr
                245                 250                 255

Ala Lys Val Leu Leu Val Arg Leu Lys Lys Thr Asp Arg Ile Tyr Ala
                260                 265                 270

Met Lys Val Val Lys Lys Glu Leu Val Asn Asp Asp Glu Asp Ile Asp
                275                 280                 285

Trp Val Gln Thr Glu Lys His Val Phe Glu Gln Ala Ser Asn His Pro
        290                 295                 300

Phe Leu Val Gly Leu His Ser Cys Phe Gln Thr Glu Ser Arg Leu Phe
```

```
             305                 310                 315                 320
        Phe Val Ile Glu Tyr Val Asn Gly Gly Asp Leu Met Phe His Met Gln
                        325                 330                 335

Arg Gln Arg Lys Leu Pro Glu Glu His Ala Arg Phe Tyr Ser Ala Glu
                    340                 345                 350

Ile Ser Leu Ala Leu Asn Tyr Leu His Glu Arg Gly Ile Ile Tyr Arg
                    355                 360                 365

Asp Leu Lys Leu Asp Asn Val Leu Leu Asp Ser Glu Gly His Ile Lys
        370                 375                 380

Leu Thr Asp Tyr Gly Met Cys Lys Glu Gly Leu Arg Pro Gly Asp Thr
        385                 390                 395                 400

Thr Ser Thr Phe Cys Gly Thr Pro Asn Tyr Ile Ala Pro Glu Ile Leu
                        405                 410                 415

Arg Gly Glu Asp Tyr Gly Phe Ser Val Asp Trp Trp Ala Leu Gly Val
                    420                 425                 430

Leu Met Phe Glu Met Met Ala Gly Arg Ser Pro Phe Asp Ile Val Gly
                    435                 440                 445

Ser Ser Asp Asn Pro Asp Gln Asn Thr Glu Asp Tyr Leu Phe Gln Val
        450                 455                 460

Ile Leu Glu Lys Gln Ile Arg Ile Pro Arg Ser Leu Ser Val Lys Ala
        465                 470                 475                 480

Ala Ser Val Leu Lys Ser Phe Leu Asn Lys Asp Pro Lys Glu Arg Leu
                        485                 490                 495

Gly Cys His Pro Gln Thr Gly Phe Ala Asp Ile Gln Gly His Pro Phe
                    500                 505                 510

Phe Arg Asn Val Asp Trp Asp Met Met Glu Gln Lys Gln Val Val Pro
                    515                 520                 525

Pro Phe Lys Pro Asn Ile Ser Gly Glu Phe Gly Leu Asp Asn Phe Asp
        530                 535                 540

Ser Gln Phe Thr Asn Glu Pro Val Gln Leu Thr Pro Asp Asp Asp Asp
        545                 550                 555                 560

Ile Val Arg Lys Ile Asp Gln Ser Glu Phe Glu Gly Phe Glu Tyr Ile
                        565                 570                 575

Asn Pro Leu Leu Met Ser Ala Glu Glu Cys Val
                    580                 585

<210> SEQ ID NO 2
<211> LENGTH: 19
<212> TYPE: RNA
<213> ORGANISM: Artificial Sequence
<220> FEATURE:
<223> OTHER INFORMATION: sequence is synthesized

<400> SEQUENCE: 2
caagccaagc guucaaca                                                     19

<210> SEQ ID NO 3
<211> LENGTH: 19
<212> TYPE: RNA
<213> ORGANISM: Artificial Sequence
<220> FEATURE:
<223> OTHER INFORMATION: sequence is synthesized

<400> SEQUENCE: 3
uguugaaacg cuuggcuug                                                    19

<210> SEQ ID NO 4
<211> LENGTH: 19
```

```
<212> TYPE: RNA
<213> ORGANISM: Artificial Sequence
<220> FEATURE:
<223> OTHER INFORMATION: sequence is synthesized

<400> SEQUENCE: 4
ggaacgauug gguugucau                                              19

<210> SEQ ID NO 5
<211> LENGTH: 20
<212> TYPE: RNA
<213> ORGANISM: Artificial Sequence
<220> FEATURE:
<223> OTHER INFORMATION: sequence is synthesized

<400> SEQUENCE: 5
augacaaccc aaucguuucc                                             20

<210> SEQ ID NO 6
<211> LENGTH: 19
<212> TYPE: RNA
<213> ORGANISM: Artificial Sequence
<220> FEATURE:
<223> OTHER INFORMATION: sequence is synthesized

<400> SEQUENCE: 6
cccaauaucu ucucuugua                                              19

<210> SEQ ID NO 7
<211> LENGTH: 19
<212> TYPE: RNA
<213> ORGANISM: Artificial Sequence
<220> FEATURE:
<223> OTHER INFORMATION: sequence is synthesized

<400> SEQUENCE: 7
uacaagagaa gauauuggg                                              19
```